United States Patent [19]
Sasse et al.

[11] 4,289,771
[45] Sep. 15, 1981

[54] 3-SULPHONYL-BENZO-1,2,4-TRIAZINE AND 3-SULPHONYL-BENZO-1,2,4-TRIAZINE 1-OXIDE COMPOUNDS, THEIR PRODUCTION AND THEIR MEDICINAL USE

[75] Inventors: Klaus Sasse, Berg.-Gladbach; Ingo Haller; Manfred Plempel, both of Wuppertal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 126,054

[22] Filed: Feb. 29, 1980

[30] Foreign Application Priority Data

Mar. 21, 1979 [DE] Fed. Rep. of Germany ....... 2910974

[51] Int. Cl.³ .................... C07D 253/08; A61K 31/53

[52] U.S. Cl. .................... 424/249; 544/183
[58] Field of Search .................... 544/183; 424/249

[56] References Cited

FOREIGN PATENT DOCUMENTS 2538179 3/1977 Fed. Rep. of Germany .
83869 8/1971 German Democratic Rep. .

Primary Examiner—John M. Ford
Attorney, Agent, or Firm—Sprung, Felfe, Horn, Lynch & Kramer

[57] ABSTRACT

The invention relates to 3-sulphonyl-benzo-1,2,4-triazines and their 1-oxides, useful as antibacterial and antifungal agents. Also included in the invention are methods for the preparation of said benzo-1,2,4-triazine compounds, pharmaceutical compositions containing said benzo-1,2,4-triazines and methods for the use of said compounds and compositions.

18 Claims, No Drawings

3-SULPHONYL-BENZO-1,2,4-TRIAZINE AND 3-SULPHONYL-BENZO-1,2,4-TRIAZINE 1-OXIDE COMPOUNDS, THEIR PRODUCTION AND THEIR MEDICINAL USE

The present invention relates to certain new 3-sulphonyl-benzo-1,2,4-triazine and 3-sulphonyl-benzo-1,2,4-triazine 1-oxide compounds, to a process for their production and to their use as antimicrobial agents with sporocidal properties.

It has already been disclosed that benzo-1,2,4-triazine 1-oxides which have halogen or an amino, hydrazino, alkoxy or alkylmercapto group in the 3-position have herbicidal, acarioidal and fungicidal properties, in this context, see German Democratic Republic Pat. No. 83,869. It is furthermore known that 3-alkoxy-benzo-1,2,4-triazines also have fungicidal and bactericidal properties, in this context see, DOS (German Published Specification) No. 2,538,179. However, such classes of compounds have only a slight action or no action at all against micro-organisms which trigger off mycotic diseases in animals, and against those which lead to infestation or destruction of organic materials.

According to the present invention there are provided compounds which are 3-sulphonyl-benzo-1,2,4-triazines and 3-sulphonyl-benzo-1,2,4-triazine 1-oxides of the general formula

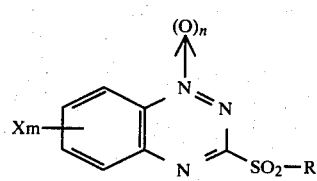

in which

X denotes a hydrogen or halogen atom or an alkyl, trifluoromethyl, alkoxy or nitro group, R denotes an alkyl group which is optionally substituted by (substituted) phenyl, halogen or alkoxy, n alkenyl or cycloalkyl group or a phenyl radical which is optionally substituted by alkyl, halogenoalkyl, halogen, alkoxy or nitro m is 1, 2, 3 or 4, and n is 0 or 1.

As used herein and unless otherwise specified, a halogen atom is preferably a chlorine, bromine or fluorine atom; an alkyl or alkoxy group preferably contains 1 to 6 carbon atoms; an alkenyl group preferably contains 2 to 6 carbon atoms; a cycloalkyl group preferably contains 4 to 7, especially 5 to 6 ring members; and a halogenoalkyl group is preferably perfluoroalkyl or perchloro alkyl in which the alkyl portion contains 1 to 2 carbon atoms.

The compounds of the present invention have powerful antimycotic properties.

According to the present invention there is further provided a process for the production of compounds of the present invention in which (a) a 3-sulphenyl-benzo-1,2,4-triazine or 3-sulphenyl-benzo-1,2,4-triazine 1-oxide of the general formula

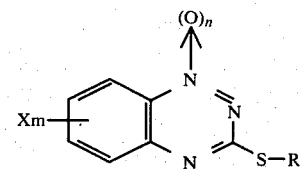

in which X, R, m and n have the above-mentioned meaning is subject to oxidation, or (b) in the case of the production of a 3-sulphonyl-benzo-1,2,4-triazine of formula (I) in which n is 0, a 3-sulphonyl-benzo-1,2,4-triazine 1-oxide of formula (I) in which n is 1 is subjected to reduction.

Surprisingly, the 3-sulphonyl-benzo-1,2,4-triazines and 3-sulphonyl-benzo-1,2,4-triazine 1-oxides according to the invention display a considerably more powerful antimicrobial action than the known benzotriazines with other substituents in the 3-position. The active compounds according to the invention also surprisingly display an additional sporocidal action on spores of fungi. The substances according to the invention thus represent an advance in pharmacy.

The process variant (a) for the production of compounds of the present invention is illustrated by the following equations in which 3-methylmercapto-7-chloro-benzo-1,2,4-triazine 1-oxide and 3-phenylmercapto-7-bromo-1,2,4-benzotriazine are reacted with oxidising agents:

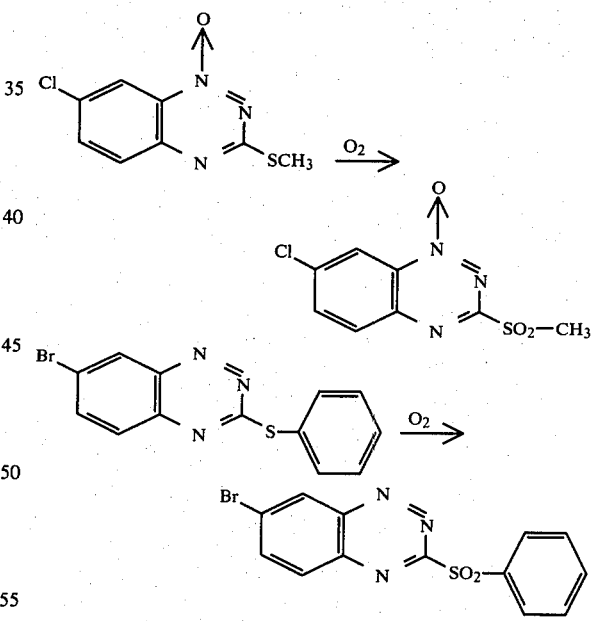

The process variant (b) is illustrated by the following equation in which 3-methylsulphonyl-7-chloro-benzo-1,2,4-triazine 1-oxide is reduced with catalytically activated hydrogen:

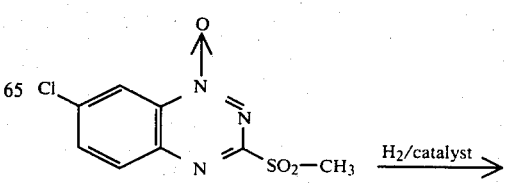

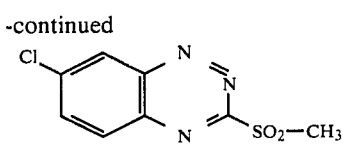

Particularly preferred compounds of the invention of Formula (I) and corresponding starting substances of formula (II) are those in which X denotes a hydrogen, chlorine or bromine atom, a trifluoromethyl group or an alkoxy group with up to 3 carbon atoms, R denotes an alkyl radical with 1 to 4 carbon atoms, a cycloalkyl radical with 5 or 6 carbon atoms, a benzyl radical which is optionally substituted by halogen, nitro or methyl, or a phenyl radical which is optionally substituted by halogen, nitro, methyl or alkoxy (with 1 to 4 carbon atoms), m has the above mentioned meaning, but is 1 or 2 if X is not hydrogen and n is 0 or 1.

The starting substances of the formula (II) are also novel. Those in which m is 1 (formula IIa) are preferably prepared by a process in which 3-chloro-benzo-1,2,4-triazine 1-oxides of the formula (III) are reacted with mercaptans of the formula (IV) in the presence of acid-binding agents:

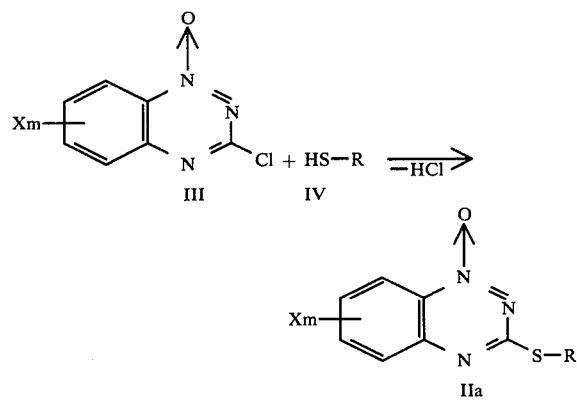

In these formulae, X, R and m have the generic or preferred meanings as indicated above.

The compounds of the formula (III) are known [in this context, see J. Org. Chem. 24, 813 (1959) and DOS (German Published Specification) No. 2,740,887].

Examples which may be mentioned are: 3-chloro-benzo-1,2,4-triazine 1-oxide, 3,6-dichloro-benzo-1,2,4-triazine 1-oxide, 3,7-dichloro-benzo-1,2,4-triazine 1-oxide, 3,5,7-trichloro-benzo-1,2,4-triazine 1-oxide, 3-chloro-7-bromo-benzo-1,2,4-triazine 1-oxide, 3-chloro-7-methyl-benzo-1,2,4-triazine 1-oxide, 3-chloro-7-methoxy-benzo-1,2,4-triazine 1-oxide, 3-chloro-7-trifluoromethyl-benzo-1,2,4-triazine 1-oxide and 3-chloro-7-nitro-benzo-1,2,4-triazine 1-oxide.

The compounds of the formula (IV) are also known (in this context, see Houben-Weyl, Methoden der organ. Chemie, Vol. IX, page 7 et seq.) Alkyl-, cycloalkyl- and benzyl-mercaptans and thiophenols which supply the desired radical R are preferably employed. As a rule, the reactants (III) and (IV) are allowed to act on one another in equimolar proportions or with a slight excess of (IV) of up to 0.25 mol. The reaction is preferably carried out in organic solvents, such as ketones (e.g. acetone, methyl ethyl ketone, etc.) and ethers, including alkyl ethers, such as dimethyl or diethyl ether and cyclic ethers, such as dioxane and tetrahydrofurane, in hydrocarbons or dimethylformamide or dimethylsulphoxide, or mixtures thereof with water. The acid-binding agents used are preferably alkali metal (preferably sodium or potassium) oxides, hydroxides, carbonates or alcoholates or alkaline earth metal (preferably calcium) oxides, hydroxides, carbonates or alcoholates. The reaction temperatures are usually 0° to 100° C.

The novel starting substances of the formula (II) in which m is 0 (formula IIb) are preferably obtained by reducing the compounds, decribed above, of the formula (IIa), wherein X, R and m have the generic or preferred meanings indicated above.

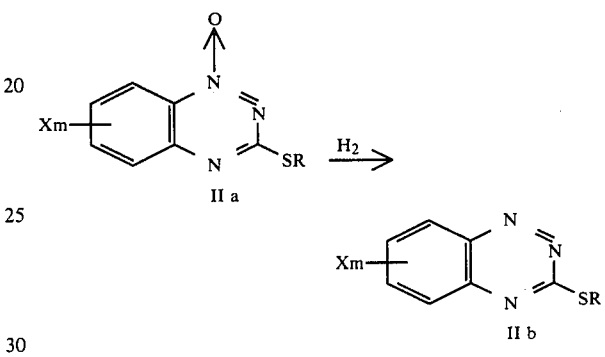

Suitable reducing agents are: zinc dust in a weakly acid medium, iron-II salts, dithionite or catalytically activated hydrogen. In the latter case, the known hydrogenation catalysts based on nickel, cobalt, palladium, platinum or rhodium are used. Raney nickel is preferably used, in amounts of 0.01 to 5 mol %. The hydrogenation is as a rule carried out in a closed vessel under a hydrogen pressure of 0 to 25 atmospheres. As in the case of the other reduction processes also, the reaction temperatures are 0° to 100° C., preferably 20° to 60° C.

Alcohols, such as alkanols of 1 to 3 carbon atoms or cyclic ethers, such as dioxane and tetrahydrofurane, are preferably used as the solvent.

The process variant (a) according to the invention comprises an oxidation. Possible oxidation processes are:

(i) Chlorine in the presence of water.

$C_1$ to $C_6$ aliphatic carboxylic acids, such as formic acid, acetic acid or propionic acid, or alcohols, such as methanol or glycol monomethyl ether, are preferably used as the solubilising agent. At least two mols of $Cl_2$ are required for quantitative reaction. As a rule, a slight excess of up to one further mol is employed. The reaction temperature is 0° to 20° C., preferably 0° to 5° C.

(ii) Hydrogen peroxide in weakly acid solution.

Acetic acid or solutions thereof diluted with water are preferred as the solvent. 2 mols of $H_2O_2$ are required for quantitative conversion. As a rule, a slight excess of up to 0.5 mol is used. The reaction temperature is 20° to 100° C., preferably 40° to 70° C.

(iii) Alkali metal permanganate

Acetic acid or solutions thereof diluted with water are preferred as the solvent. 1.34 mols of $KMnO_4$, for example, are required for quantitative conversion. As a rule, an excess of up to a further 0.25 mol is also used in this case. The reaction temperatures are 0° to 100° C., preferably 10° to 50° C. Before working up the reaction batches, it is advisable to reduce the permanganate which has not been consumed and the manganese-IV oxide formed to $Mn^{+2}$ by adding salts of sulphurous acid.

The process variant (b) according to the invention comprises a reduction stage which is carried out as described above for the intermediate products of the formula (IIb), that is to say the reduction is carried out under the conditions indicated above, with zinc dust in a weakly acid medium, with iron-II salts or dithionite or (preferably) with catalytically activated hydrogen.

Particularly preferred compounds of the present invention are: -3-methylsulphonyl-benzo-1,2,4-triazine, 3-methylsulphonyl-benzo-1,2,4-triazine 1-oxide, 3-methylsulphonyl-7-chloro-benzo-1,2,4-triazine, 3-methylsulphonyl-7-chloro-benzo-1,2,4-triazine 1-oxide, 3-ethylsulphonyl-7-chloro-benzo-1,2,4-triazine 1-oxide, 3-butylsulphonyl-7-chloro-benzo-1,2,4-triazine 1-oxide, 3-cyclohexylsulphonyl-7-chloro-benzo-1,2,4-triazine 1-oxide, 3-benzylsulphonyl-7-chloro-benzo-1,2,4-triazine 1-oxide, 3-(4-chlorobenzylsulphonyl)-7-chloro-benzo-1,2,4-triazine 1-oxide, 3-(4-methylbenzylsulphonyl)-7-chloro-benzo-1,2,4-triazine 1-oxide, 3-(3-nitro-benzylsulphonyl)-7-chloro-benzo-1,2,4-triazine 1-oxide, 3-phenylsulphonyl-7-chloro-benzo-1,2,4-triazine 1-oxide, 3-(4-methyl-phenylsulphonyl)-7-chloro-benzo-1,2,4-triazine 1-oxide, 3-(4-chloro-phenylsulphonyl)-7-chloro-benzo-1,2,4-triazine 1-oxide, 3-(4-methoxy-phenylsulphonyl)-7-chloro-benzo-1,2,4-triazine 1-oxide, 3-(4-nitro-phenylsulphonyl)-7-chloro-benzo-1,2,4-triazine 1-oxide, 3-methylsulphonyl-5,7-dichloro-benzo-1,2,4-triazine 1-oxide, 3-phenylsulphonyl-5,7-dichloro-benzo-1,2,4-triazine 1-oxide, 3-methylsulphonyl-7-bromo-benzo-1,2,4-triazine 1-oxide, 3-phenylsulphonyl-7-bromo-benzo-1,2,4-triazine 1-oxide, 3-methylsulphonyl-7-trifluoromethyl-benzo-1,2,4-triazine 1-oxide, 3-methylsulphonyl-7-methoxy-benzo-1,2,4-triazine 1-oxide and 3-methylsulphonyl-7-nitro-benzo-1,2,4-triazine 1-oxide.

The compounds of the present invention display powerful antimicrobial actions, in particular antimycotic actions. They exhibit a broad action spectrum in vitro, which includes dermatophytes, yeasts, moulds and biphase fungi. It should be emphasised in particular that they have a good and rapid sporocidal activity against spores of fungi.

Examples which may be mentioned of fields of indication in medicine are: dermatomycoses and systemic mycoses caused by Trichophyton mentagrophytes and other varieties of Trichophyton, varieties of Microsporon, Epidermophyton floccosum, blastomyces and biphase fungi, as well as moulds. The active compounds according to the invention also have a powerful antibacterial activity, coupled with a low toxicity and a good level of tolerance.

The properties mentioned also enable the new compounds to be used as active compounds, having a prophylactic action and a preventive action against fungal attack, in the protection of materials, as well as in medicine, and for preserving all types of inorganic and organic materials.

Examples of materials which can be adversely effected by fungal growth are; white washes, emulsion paints, wallpapers, joints of tiled walls, furniture, leather, imitation leather, plastics, rubber, bath mats, shower curtains, textiles, carpets and tent equipment.

Examples of, in particular, organic materials suitable for preservation are; polymers, lubricants paints, fibres, leather, paper and wood, and also foodstuffs and cosmetics, such as creams and ointments. Water may also be preserved.

The active compounds according to the invention are active against a very broad spectrum of microorganisms. They can be used, for example, to combat Gram-negative and Gram-positive bacteria and bacteria-like micro-organisms and to prevent, alleviate and/or cure illnesses caused by these pathogens.

The active compounds according to the invention are particularly active against bacteria and bacteria-like micro-organisms. They are therefore particularly suitable for the prophylaxis and chemotherapy of local and systemic infections, caused by these pathogens, in human medicine and veterinary medicine.

For example, local and/or systemic illnesses caused by the following pathogens or by mixtures of the following pathogens can be treated:

Micrococcaceae, such as Staphylococci, for example Staphylococcus aureus and Staph, epidermidis;

Lactobacteriaceae, such as Streptococci, for example *Streptococcus phygens*, α- or β-haemolysing Streptococci, non(τ)-haemolysing Streptococci, *Str. viridans* and *Str. Faecalis* (Enterococci);

Corynebacteriaceae, such as Corynebacteria, for example *Corynebacterium diphtheriae, C. pyogenes, C. diphtheroides, C. acnes* and *C. parvum;*

Enterobacteriaceae, such as Escherichiae bacteria of the coli group: Escherichia bacteria, for example *Escherichia coli,* Klebsiella bacteria, for example *K. pneumoniae,* and Proteae bacteria of the Proteus group: Proteus, for example *Proteus vulgaris* and *Pr. mirabilis,* and Pseudomonadaceae, such as Pseudomonas bacteria, for example *Pseudomonas aeruginosa.*

The above list of pathogens is purely illustrative and is in no way to be interpreted as restrictive.

The following may be mentioned as examples of illnesses which can be treated by the active compounds according to the invention:

illnesses of the respiratory passages and of the pharyngeal cavity; otitis; pharyngitis; pyelonephritis; cystitis; and local infection, for example of the skin and of mucous membranes which can be reached by a local method.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form"

as used in this Specification means physically discrete coherent units suitable for medical administration each containing a daily does or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacificers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parental administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delated release of the active ingredient. Some, such as capsules, include a protective envelope which renders the portions of the medicament physically discrete and coherent.

The preferred daily dose for administration of the medicaments of the invention is 2.5 to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

In general it has proved advantageous to administer amounts of from 10 mg to 300, preferably 50 mg to 200 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

For use in the industrial field or in the hygiene sector, the active compounds according to the invention can be employed in the unmodified form or with a carrier, for example dispersed on a fine-particled solid, or as a dust. Such mixtures can also be dispersed in water, with the aid of a wetting agent, and the resulting emulsions can be used as a spray. In other procedures, the products can be used as active compounds in solvent solutions or oil-in-water or water-in-oil emulsions. The mixtures can be formulated as concentrates and then diluted with further liquid or solid auxiliaries in order to prepare the final treatment mixture. Good results are obtained, in particular, if mixtures containing 0.5 to 3% of active compound are used.

The following Examples A, B and C illustrate the in vitro activity of compounds of the present invention.

EXAMPLE A

Antimycotic in vitro activity

Description of the experiment:

The minimum inhibitory concentrations (MIC) against fungi are determined in a series dilution test with germ inocula of an average of $5 \times 10^4$ germs/ml of substrate. The nutrient medium used is (a) for dermatophytes and moulds: sabourand's milieu d'épreuve and (b) for yeasts: meat extract/glycose broth.

The incubation temperature is 28° C. and the duration of incubation is 24 to 96 hours.

The results show a high antimycotic action.

EXAMPLE B

Antibacterial in vitro activity

Description of the experiment:

The minimum inhibitory concentration against bacteria are determined in an agar dilution test. For this test, various concentrations of preparation are suspended in liquid DST-agar medium, together with the test strain, and the suspensions are poured into Petridishes (diameter: 5 cm). The germ inoculum per plate is $5 \times 10^3$ germs. The lowest concentration of preparation at which no further colony formation takes place within 24 hours is called the MIC.

The results show a high antibacterial action.

EXAMPLE C

Sporocidal activity

Description of the experiment:

Spore suspensions in physiological sodium chloride solution are prepared which contained about $10^6$ microconidia of Trichophyton mentagrophytes per ml. After adding, 10, 50 and 100 mcg/ml of active compound, these spore suspensions are incubated at 28° C.; after 24, 48, 96, 120 and 240 hours, samples are taken, diluted in the ratio 1:1,000 and then smoothed out homogeneously on malt extract agar plates. After incubation at 28° C. for 3 days, the colonies of fungus on these agar plates are counted as a measure of the bumber of spores capable of germination. The evaluation takes place in comparison to germ controls without an active compound.

Results:

The active compound of the following Examples 6, 12 and 15 show a very good sporocidal action each in concentrations of 10 mcg/ml: after a period of action of 24 hours, all the spores which had been employed are killed or incapable of germination.

The following Examples 2 to 15 illustrate the preparation of compounds of the present invention and Example 1 illustrates the preparation of precursors.

EXAMPLE 1

Precursor A

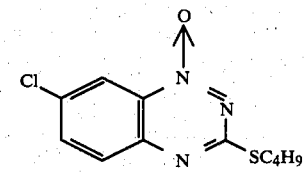

21.6 g. of 3,7-dichloro-benzo-1,2,4-triazine 1-oxide are introduced in portions into a mixture of 9 g (0.1 mol) of butylmercaptan, 9.1 g (0.1 mol) of concentrated sodium hydroxide solution and 100 ml of dioxane at room temperature, whilst cooling slightly. The reaction mixture is subsequently stirred at room temperature for a further 1 hour and at 50° C. for 2 hours and then poured into water. The initially oily precipitate crystallises when cooled for a prolonged period. The crystals are filtered off and recrystallised from a little wash benzine. 22.7 g (84% of theory) of 7-chloro-3-butylmercapto-benzo-1,2,4-triazine 1-oxide of melting point m.p.:58°–60° are obtained.

The following compounds are prepared in a corresponding manner:

| X | Y | R | Melting point °C. | Recrystallised from |
|---|---|---|---|---|
| Cl | H | CH₃ | 137–138 | wash benzine |
| Cl | H | CH₂–⟨phenyl⟩ | 101–102 | wash benzine |
| Cl | H | ⟨phenyl⟩ | 187–188 | Toluene |
| Cl | Cl | CH₃ | 145–146 | Tetra*/ligroin |
| Cl | Cl | C₄H₉ | 54–55 | wash benzine |
| Cl | Cl | ⟨phenyl⟩ | 155–156 | wash benzine |
| Br | H | CH₃ | 142–143 | wash benzine |
| F₃C | H | CH₃ | 111–112 | wash benzine |

*The word "tetra" used here and elsewhere in the Examples stands for carbon tetrachloride.

Precursors B

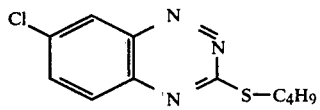

A solution of 27.0 g (0.1 mol) of 7-chloro-3-butylmercapto-benzo-1,2,4-triazine 1-oxide in 175 ml of dioxane is initially introduced into a VA stirred autoclave with 5 g of Raney nickel. Hydrogen is forced in to a pressure of 15 atmospheres at 30° C. The mixture is subsequently stirred at 30°-50° C. for 5 hours, and during this procedure further hydrogen is forced in until the pressure remains constant. The pressure is let down, the catalyst is filtered off and the filtrate is evaporated in vacuo. The residue is recrystallised from ligroin. 8 g (85% of theory) of 7-chloro-3-butylmercapto-benzo-1,2,4-triazine of melting point m.p.: 66°-68° C. are obtained.

The following compounds are obtained in an analogous manner:

| | Melting point | Recrystallised |
|---|---|---|

EXAMPLE 2

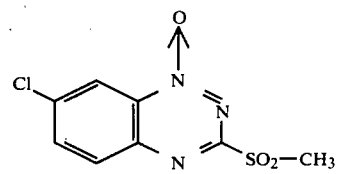

22.8 g (0.1 mol) of 7-chloro-3-methylmercapto-benzo-1,2,4-triazine 1-oxide are suspended in a mixture of 200 ml of acetic acid and 60 ml of water. Chlorine is passed in, whilst maintaining a temperature of 0°-5°, until the mixture is saturated. The excess chlorine is then removed by passing nitrogen in. The reaction mixture is diluted with 1 liter of water. The crystals which have separated out are filtered off and recrystallised from a little toluene. 18.7 g (72% of theory) of 7-chloro-3-methylsulphonyl-benzo-1,2,4-triazine 1-oxide of melting point m.p.:213°-214° are obtained.

The following compounds are obtained in an analogous manner:

| Example No. | X | Y | R | Melting point °C. | Recrystallised from |
|---|---|---|---|---|---|
| 2a | Cl | H | C$_3$H$_7$ | 198–200 | toluene |
| 3 | Cl | H | C$_4$H$_9$ | 160 | butanol |
| 4 | Cl | H | CH$_2$—⌬ | 105–106 | wash benzine |
| 5 | Cl | H | —⌬ | 202–204 | toluene |
| 5a | Cl | H | —⌬—Cl | 210–212 | wash benzine |
| 5b | Cl | H | —⌬—CH$_3$ | 248–250 | toluene |
| 5c | Cl | H | —⌬—C(CH$_3$)$_3$ | 210–212 | wash benzine |
| 6 | Cl | Cl | CH$_3$ | 168–170 | ethyl acetate/ligroin |
| 7 | Cl | Cl | C$_4$H$_9$ | 113–114 | ethanol |
| 8 | Cl | Cl | —⌬ | 199–200 | toluene |
| 9 | Br | H | CH$_3$ | 228–230 | dioxane |
| 10 | F$_3$C | H | CH$_3$ | 189–190 | toluene |

| X | Y | R | °C. | from |
|---|---|---|---|---|
| Cl | H | CH$_3$ | 105–106 | toluene |
| Cl | H | —⌬ | 155–156 | toluene |
| Cl | Cl | CH$_3$ | 146–148 | tetra/Ligroin |
| Br | H | CH$_3$ | 108–110 | wash benzine |

EXAMPLE 11

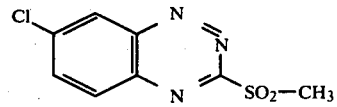

21.2 g (0.1 mol) of 7-chloro-3-methylmercapto-benzo-1,2,4-triazine are suspended in a mixture of 300 ml of acetic acid and 120 ml of water. Gaseous chlorine is passed in at 0°-5° until the mixture is saturated. The mixture is subsequently stirred at the same temperature for a further 2 hours and excess chlorine is then removed by bubbling nitrogen in. The reaction mixture is diluted with 1 liter of water and the crystalline product is filtered off. After recrystallisation from ethanol, 19 g (73.5% of theory) of 7-chloro-2-methylsulphonyl-benzo-1,2,4-triazine of melting point m.p.:147°–148° are obtained.

The following compounds are obtained in a corresponding manner:

[Structure: X and Y substituted benzo-1,2,4-triazine with SO$_2$–R]

| Example No. | X | Y | R | Melting point °C. | Recrystallised from |
|---|---|---|---|---|---|
| 12 | Cl | H | C$_4$H$_9$ | 90–92 | wash benzine |
| 13 | Cl | H | –⟨phenyl⟩ | 169–170 | toluene |
| 14 | Cl | Cl | CH$_3$ | 137–138 | toluene |
| 15 | Br | H | CH$_3$ | 167–168 | ethyl acetate |

The present invention also comprises pharmaceutically acceptable bioprecursors of the active compounds of the present invention.

For the purposes of this specification, the term 'pharmaceutically acceptable bioprecursor' of an active compound of the invention means a compound having a structural formula different from the active compound but which nonetheless, upon administration to an animal is converted in the patient's body to the active compound.

What is claimed is:

1. A compound which is a 3-sulphonyl-benzo-1,2,4-triazine or 3-sulphonyl-benzo-1,2,4-triazine 1-oxide of the formula $$\text{(I)}$$

in which
X is a hydrogen or halogen atom or an alkyl, trifluoromethyl, alkoxy or nitro group,
R is an alkyl group which is optionally substituted by phenyl optionally substituted by halogen, nitro or methyl, halogen, or alkoxy, an alkenyl or cycloalkyl group or a phenyl radical which is optionally substituted by alkyl, halogenoalkyl, halogen, alkoxy or nitro,
m is 1, 2, 3, or 4, and
n is 0 or 1.

2. A compound according to claim 1 in which X is a hydrogen, chlorine or bromine atom, a trifluoromethyl group with up to 3 carbon atoms, R is an alkyl radical with 1 to 4 carbon atoms, a cycloalkyl radical with 5 or 6 carbon atoms, a benzyl radical which is optionally substituted by halogen, nitro or methyl, or a phenyl radical which is optionally substituted by halogen, nitro, methyl or alkoxy (with 1 to 4 carbon atoms) m has the same meaning as in claim 1 but is 1 or 2 if X is not hydrogen and n is 0 or 1.

3. A compound according to claim 1 which is 7-chloro-3-methylsulphonyl-benzo-1,2,4-triazine 1-oxide.

4. A compound according to claim 1 which is 7-chloro-3-benzylsulphonyl-benzo-1,2,4-triazine 1-oxide.

5. A compound according to claim 1 which is 7-chloro-3-phenylsulphonyl-benzo-1,2,4-triazine 1-oxide.

6. A compound according to claim 1 which is 5,7-dichloro-3-phenylsulphonyl-benzo-1,2,4-triazine 1-oxide.

7. A compound according to claim 1 which is 7-trifluoro-methyl-3-methylsulphonyl-benzo-1,2,4-triazine 1-oxide.

8. A compound according to claim 1 which is 7-chloro-2-methylsulphonyl-benzo-1,2,4-triazine.

9. A compound according to claim 1 which is 7-bromo-2-methylsulphonyl-benzo-1,2,4-triazine.

10. A process for the production of a compound of claim 1 having the formula $$\text{(I)}$$

which comprises oxidizing the sulphenyl group to a sulphonyl group in the 3-sulphenyl-benzo-1,2,4-triazine or 3-sulphenyl-benzo-1,2,4-triazine 1-oxide of the formula $$\text{(II)}$$

wherein X, R, m and n have the same meanings as in claim 1, said oxidation of the sulphenyl to sulphonyl groups being effected by (i) chlorine in the presence of water, (ii) hydrogen peroxide in weakly acid solution or (iii) alkali metal permanganate.

11. A process according to claim 10 in which the oxidation is carried out with chlorine in the presence of water at 0° to 5° C., with hydrogen peroxide in weakly acid solution at 40° to 70° C., or with alkali metal permanganate at 10° to 50° C.

12. A pharmaceutical composition containing as an active ingredient an antimicrobially effective amount of a compound according to claim 1 in admixture with a solid, liquid or liquefied gaseous diluent.

13. A pharmaceutical composition according to claim 12 in the form of a sterile or physiologically isotonic aqueous solution.

14. A medicament in dosage unit form comprising an antimicrobially effective amount of a compound according to claim 1 together with an inert pharmaceutical carrier.

15. A medicament of claim 14 in the form of tablets, pills, dragees, capsules, ampoules, or suppositories.

16. A method of combating microbial illnesses in warmblooded animals which comprises administering to the animals an antimicrobially effective amount of a compound according to claim 1 either alone or in admixture with a diluent or in the form of a medicament.

17. A method according to claim 16 in which the active compound is administered in an amount of 10 to 300 mg per kg body weight per day.

18. A method according to claim 17 in which the active compound is administered in an amount of 50 to 200 mg per kg body weight per day.

* * * * *